United States Patent [19]

Wittkampf et al.

[11] Patent Number: 4,644,954

[45] Date of Patent: Feb. 24, 1987

[54] RATE ADAPTIVE PACEMAKER APPARATUS AND METHOD

[75] Inventors: Frederik H. M. Wittkampf, LK Brummen, Netherlands; Anthony F. Rickards, Chalcot Park, England

[73] Assignee: Vitafin N.V., Curacao, Netherlands

[21] Appl. No.: 745,836

[22] Filed: Jun. 18, 1985

Related U.S. Application Data

[63] Continuation of Ser. No. 569,670, Jan. 10, 1984, abandoned.

[51] Int. Cl.[4] ............................................. A61N 1/36
[52] U.S. Cl. ................................................. 128/419 PG
[58] Field of Search ................................. 128/419 PG

[56] References Cited

U.S. PATENT DOCUMENTS

| | | | |
|---|---|---|---|
| 3,921,642 | 11/1975 | Prestow et al. | 128/419 PG |
| 4,228,803 | 10/1980 | Rickards | 128/419 PG |
| 4,284,082 | 8/1981 | Funke et al. | 128/419 PG |
| 4,298,007 | 11/1981 | Wright et al. | 128/419 PG |
| 4,305,396 | 12/1981 | Wittkampf et al. | 128/419 PG |
| 4,401,119 | 8/1983 | Herpers | 128/419 PG |

OTHER PUBLICATIONS

Rickards et al, "Pace", V. G., Part II, Mar.-Apr. 1983, pp. 346-354.

Primary Examiner—William E. Kamm
Attorney, Agent, or Firm—Woodcock Washburn Kurtz Mackiewicz & Norris

[57] ABSTRACT

A pacemaker and method of cardiac pacing employing the Tx mode of rate control, having means for automatically terminating the refractory period after sensing of an evoked T wave following a delivered stimulus. The pacemaker also is capable of overriding a natural rate and delivering one or more stimulus pulses so as to obtain a Tx rate determination during what would otherwise be inhibited pacer operation.

9 Claims, 5 Drawing Figures

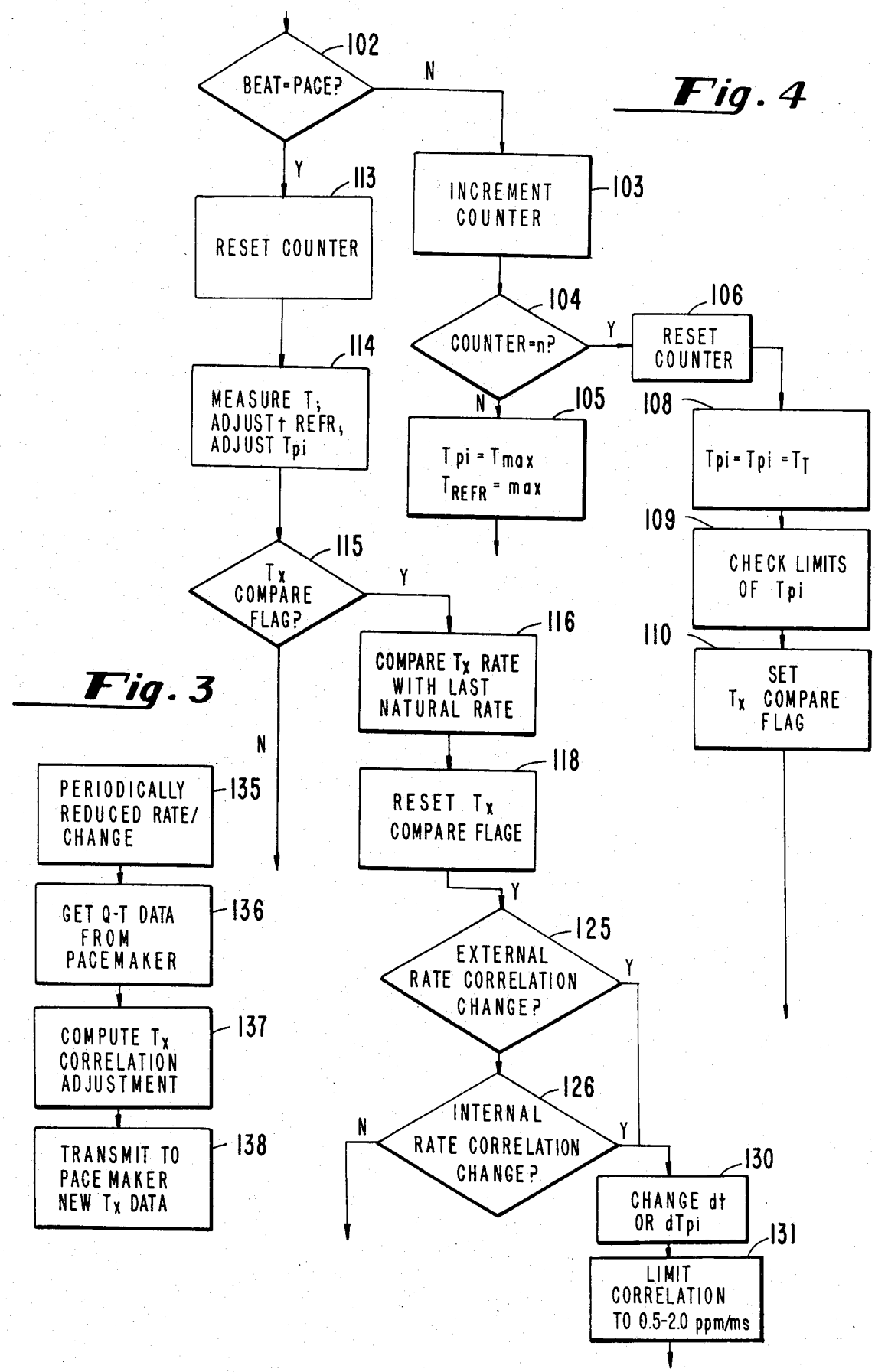

RATE ADAPTIVE PACEMAKER APPARATUS AND METHOD

This is a continuation of application Ser. No. 569,670, filed Jan. 10, 1984, now abandoned.

BACKGROUND OF THE INVENTION

This invention relates to a rate adaptive pacemaker and, more particularly, to a pacemaker employing the Tx principle of controlling rate as a function of sensed stimulus-T wave interval.

A physiologically adaptive cardiac pacemaker, wherein the desired pacing rate is determined as a function of sensed stimulus-T wave (Q-T) interval has been shown in U.S. Pat. No. 4,228,803, Rickards. This pacemaker, which is now being produced commercially, is referred to as the Tx rate adaptive pacemaker. The use of a microprocessor, or equivalent programmable circuitry in a pacemaker, such as shown in EPO Application No. 81108940.8, makes the Tx pacer more readily feasible. Other improvements to this principle are disclosed in U.S. Pat. No. 4,305,396, Wittkampf et al.

The Tx rate adaptive pacer makes possible an improvement in determining the refractory interval for a ventricular (or atrial) pacer which has not been heretofore available. In conventional pacemakers, it is necessary to set the refractory interval safely after the expected time of occurrence of the T wave. However, this safety factor is at the expense of QRS sensing, since a longer refractory period results in a shorter sense period. In the Tx pacer, however, the occurrence of the T wave is sensed, and accordingly information is readily available for terminating the refractory period directly after the sensed T wave.

A normal premise of a rate adaptive demand pacemaker, Tx or otherwise, is that when the natural patient heart rate is being sensed and the pacemaker stimulus delivery is being inhibited, an optimum condition obtains. In other words, when the heart is able to operate without intervention of the pacemaker, it should do so. However, at the same time, there may be conditions when the pacemaker should overtake or overdrive the natural rate. For the Tx pacer, as long as pacing is inhibited, no Q-T data is acquired from which a pacing rate can be determined. Under such circumstances, it is desirable to get the Q-T rate indication and adjust the pacing rate, either to overtake the heart or to have the proper pacing rate established in the event of loss of the natural beat.

Another need of adaptive rate pacers generally is that of periodically checking and adjusting the correlation between a pacer indicated rate and the sensed physiological parameter, or data. For example, for the Tx pacer, a correlation or sensitivity function in terms of beats per minute (bpm) per Q-T interval (ms) must be programmed into the microprocessor; it is desirable to be able to check that correlation function and determine, at any point in the lifetime of the implanted pacemaker, whether the correlation function is appropriate, or whether it should be adjusted in view of data concerning the patient.

SUMMARY OF THE INVENTION

It is an object of this invention to provide an improved Tx rate adaptive pacemaker and method of pacing operation, whereby the cycle-to-cycle occurrence of the evoked T wave is tracked with a time-adjustable window and the refractory interval is adjusted optimally in relation to the T wave.

It is another object of this invention to provide a rate adaptive pacemaker with automatic means for adjusting the correlation between indicated pacing rate and sensed patient parameter data.

It is another object of this invention to provide a Tx type rate adaptive pacemaker with means for acquiring patient data and adjusting the correlation factor of indicated rate per Q-T interval according to such data.

It is another object of this invention to provide a rate adaptive pacemaker with means for measuring threshold changes in a rate-indicating body parameter, such as Q-T interval, and adjusting pacing rate as a function of such threshold changes.

It is yet another object of this invention to provide a Tx type rate adaptive pacemaker with means for delivering early stimulus pulses to interrupt inhibited operation, thereby to obtain rate indicating data with which to evaluate a sensed natural heartbeat rate.

In accordance with the above objects, a demand pacemaker with Tx type adaptive rate control is provided with means for tracking the T wave and ending the refractory period upon sensing the T wave. In order to check whether natural heartbeats which cause inhibited operation are acceptable, means are provided for delivering one or more early stimuli and for comparing the natural rate with the Tx indicated rate, and for making an appropriate response to the comparison. The pacemaker also has means for checking and adjusting the programmed correlation factor between indicated rate and Q-T interval.

BRIEF DESCRIPTION OF THE DRAWINGS

FIG. 3 is a flow diagram illustrating steps for checking the Tx correlation factor.

FIG. 4 is a flow diagram of a software program useful in this invention, incorporating means for changing the correlation factor between the pacing rate and sensed Q-T interval and for testing whether the patient natural rate is physiological or pathological.

DESCRIPTION OF THE PREFERRED EMBODIMENT

Figure 1:
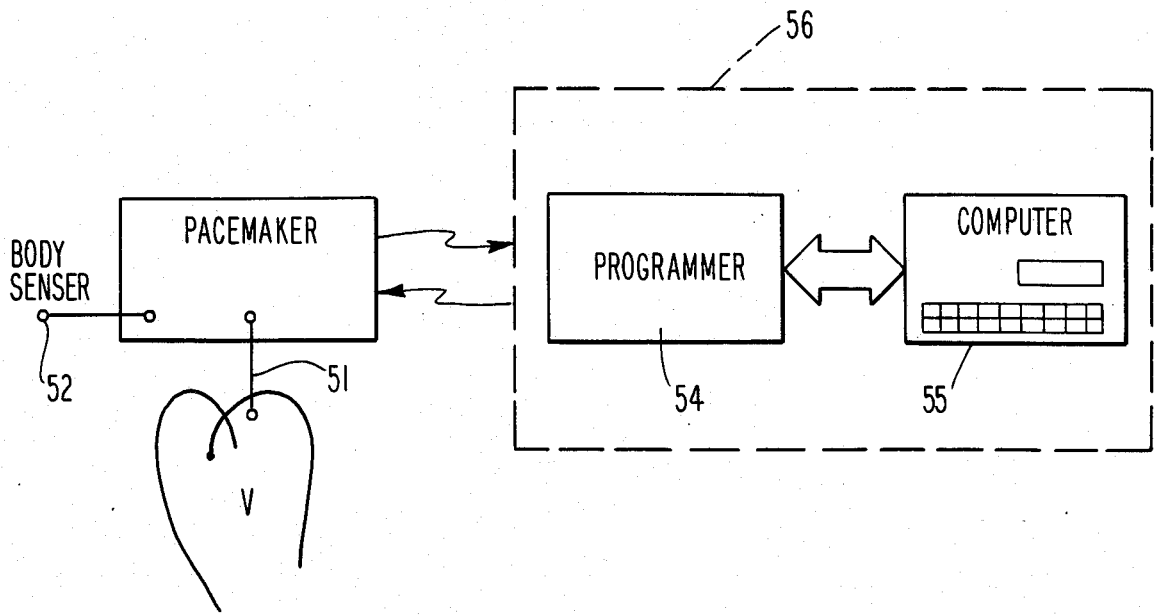
FIG. 1 is a block diagram of a pacing system including an implantable pacemaker and external programming apparatus, as used in this invention.

Reference is made to EPO application No. 81108940.8 incorporated herein by reference, which shows in detail an implantable pacemaker utilizing a microprocessor. As disclosed in the referenced application, the microprocessor pacemaker provides great flexibility, and different operating modes and routines can be easily incorporated by storing appropriate software in the pacemaker. As illustrated in the referenced application, and also as detailed in U.S. application Ser. No. 465,891, incorporated by reference, data may be transmitted between an external programmer to the pacemaker. Such external programming is now state of the art, and preferably part of the overall system into which this invention is incorporated, as illustrated in FIG. 1. The implantable pacemaker 50 is shown in two-way communication with external programming means 56.

The external programming apparatus suitably comprises a programmer 54 which is positioned adjacent to the patient's heart, the programmer being in two-way communication with a computer 55, suitably an HP 85 computer. By this means, the operator can obtain operating data from the pacemaker and reprogram pacing variables in response thereto. Further, due to the memory capacity of the pacemaker, it is a relatively simple task to enable the pacemaker to operate in a number of different modes.

While the pacemaker of this invention is illustrated as being a simple single chamber, i.e., ventricular pacer, with a lead 51 connecting the pacemaker and the patient's ventricle, it is to be understood that the invention is applicable to atrial and dual chamber pacers. Also, there is illustrated a body sensor 52, which may be utilized to sense another body parameter such as respiration rate, the body parameter data being used for rate control purposes. More specifically, in the preferred embodiment of this invention, the pacemaker is a Tx type rate adaptive pacemaker such as disclosed in U.S. Pat. No. 4,228,803, incorporated herein by reference. In such a pacemaker, the time interval from the delivered stimulus to the measured evoked T wave, referred to as the Q-T interval, is taken as an indicator of desired pacing rate, and means are provided for adjusting or controlling the pacing rate in terms of the sensed Q-T interval. As used herein, the phrase Q-T refers to either the time interval between a delivered stimulus and evoked T-wave when the pacemaker is pacing, or the time interval between the natural QRS and the T wave which follows, during pacemaker inhibited operation.

Figure 2B:
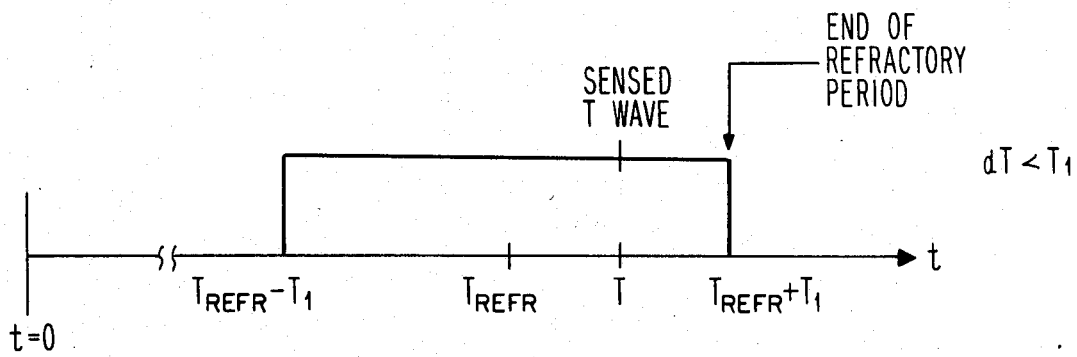
FIG. 2b is a timing diagram illustrating the T wave detection window used in the Tx embodiment of this invention.
Figure 2A:
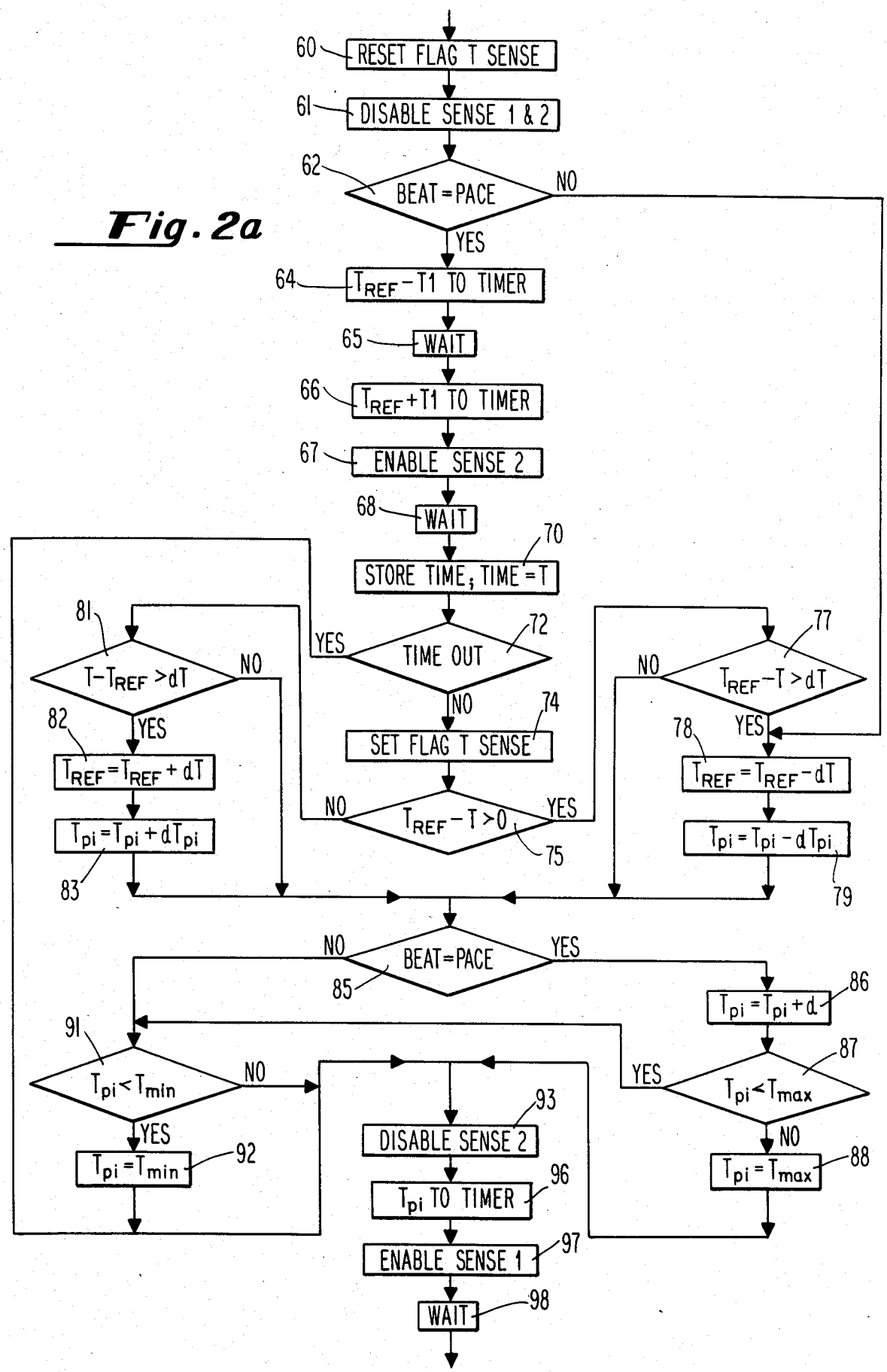
FIG. 2a is a flow diagram of a Tx pacer with adjustable T wave sensing window and overdrive means.

Referring to FIG. 2a, there is shown a flow diagram which illustrates an improved form of Tx operation, wherein there is an incorporated an "overdrive" feature such that when inhibited operation is recognized the pacing interval is incrementally decreased until one or more stimulus signals are delivered, thereby enabling determination of the Tx-indicated rate. This procedure overcomes the problem that we have observed, namely that during inhibited operation the pacemaker is not receiving Q-T data, and as a result it lacks feedback as to whether the natural rate is physiologically good.

As illustrated, the flow diagram of FIG. 2a runs during the refractory period and starts just after pulse delivery or inhibition (not shown). As used in the flow diagram, the term "wait" means that the microprocessor is turned off and waits for start-up either by sensing an event or by timing out. Each block which indicates that a certain time is sent to the timer means that the pacemaker next looks for that time in the course of the pacing cycle.

At block 60, the pacemaker resets the T sense flag, and at block 61 disables the sense circuits 1 and 2, for sensing QRS and T waves respectively. At 62, the pacemaker determines whether the last interval was ended with a natural beat or a delivered stimulus pulse. If beat=pace, meaning that a stimulus was delivered, the pacemaker proceeds to set up the T wave window at block 64–68. Referring also to FIG. 2b, the pacemaker first puts the time $T_{ref}-T_1$ to the timer, which represents the start of the T wave window. At block 65, the pacemaker waits for that time to time out, and then sets the back edge of the window, $T_{ref}+T_1$ to the timer at block 66, and enables the T wave sensing circuit at block 67. At block 68, the pacemaker waits, meaning that it is waiting through the time period of the window as illustrated in FIG. 2b. The wait is interrupted either by time out or a sensed T wave. At block 70 the pacemaker stores the time T, which represents the QT interval since the timing of the cycle starts at the time of ventricular stimulus or inhibition. At block 72, it is determined whether there has been a time out; if yes, the pacer branches to block 93.

If the determination at block 72 is that there has been no time out, meaning that the T wave was sensed, the T sense flag is set at block 74. It is next determined whether $T_{ref}-T$ is greater than 0, i.e., whether the sensed T wave arrived in the first half or second half of the window. If the answer is yes, meaning that the T wave was sensed in the first half of the window, the program branches to block 77. It is then determined whether the difference is greater than a predetermined incremental value dT which may typically be 0.7 ms. If no, the program branches to block 85. If yes, the program goes to block 78 and subtracts the value of dT from $T_{ref}$. At block 79, the pacing interval $T_{pi}$ is reduced by a value $dT_{pi}$, suitably 6 ms. Thus, in response to the sensing of the QT interval having a decrease by more than an incremental amount, the T sense window is shifted minus dT and the pacing interval is reduced by the value $T_{pi}$. The values of dT and $dT_{pi}$ determine the slope setting, or the correlation factor between QT time and indicated change in pacing rate. A normal setting of a slope of 1 ppm/ms gives dT=0.7 ms and $dT_{pi}$=6 ms, calculating the correlation value at a rate of 85 ppm. In the practice of this invention it has been found that the slope or correlation factor should be maintained within the range of 0.5 to 2.0, in order to provide good rate tracking.

Returning to block 75, if the answer is no, meaning that the T wave was sensed after the middle of the window, then at block 81 it is determined whether the difference between T and $T_{ref}$ is greater than dT. Again, if the answer is no, meaning that the change in QT interval was less than dT, the program branches to block 85. If the answer is yes, $T_{ref}$ is incremented by +dT, and $T_{pi}$ is incremented by $+dT_{pi}$.

At block 85, it is determined whether the last cycle was ended with a delivered pacing stimulus. If yes, the program branches to block 86 and adds an increment d to the pacing interval. This provides a normal downward drift in pacing rate, when the pacemaker is delivering stimulus pulses. Note that if the sensed QT interval in subsequent cycles continues to indicate a higher rate, the timing change at block 78 will maintain the higher rate. However, in the absence of such QT information, the pacing rate will gradually drift downward to a predetermined minimum or base rate. At block 87, it is determined whether $T_{pi}$ is less than the maximum pacing interval $T_{max}$; if not, $T_{pi}$ is set equal to $T_{max}$ at 88. If yes, the program branches to blocks 91 and 92, where the pacing rate is tested with respect to the minimum spacing interval $T_{min}$. Note also that if, at block 85, it is determined that the last interval was terminated with a sensed QRS, the program likewise branches to block 91. Following this, at block 93 the sense 2 circuit for detecting the T wave is disabled. At block 96, the pacing interval $T_{pi}$ is set to the timer, the sense 1 (QRS) circuit is enabled at 97, and at 98 the microprocessor waits until the next ventricular event initiates the new cycle. Note that if a T wave is sensed, the microprocessor handles certain steps and then the QRS sense is enabled at block 97, i.e., the refractory period is terminated upon sensing of the T wave. Alternately, upon detection of a T wave the pacer can still wait for time out of the refractory interval, if desired, before setting $T_{pi}$ to the timer and enabling the QRS sense.

It is recognized that the correlation factor between Q-T and change in pacing rate may require adjustment following a certain length of pacing operation. Such adjustment may be made either through the external programming means as illustrated by the flow diagram of FIG. 3, or may be made automatically by internal analysis. In FIG. 3, at block 135 the operator takes steps to periodically induce a rate change in the patient, by known means. At block 136, the pacemaker outputs QT data to the apparatus 56, where it is examined by the operator. At block 137, either the operator or the computer 55 computes the desired Tx correlation adjustment, and the Tx adjustment data is transmitted back to the pacemaker at block 138.

Referring now to FIG. 4, there is illustrated a flow diagram of another embodiment of this invention, for automatically comparing a sensed patient natural rate with the indicated Tx rate. In this flow diagram some of the details shown in FIG. 2a are omitted for brevity. At block 102, it is determined whether the last cycle ended with a pacing stimulus. If yes, a counter for counting successive natural sensed heartbeats is reset at block 113. At block 114, the steps for measuring the QT interval are carried out, and the pacing rate is adjusted accordingly. At block 115, the microprocessor determines whether there is a Tx compare flag, i.e., whether the program is to compare the Tx indicated rate with the last natural rate. If not, the routine carries out the limit checks as shown in FIG. 2a, and exits. If, at block 115, it is found that the Tx compare flag is set, then at block 116 the microprocessor compares the Tx indicated rate with the last natural rate. This is a programmed logical step and may, for example, be a comparison of the difference of the Tx rate and the natural rate with a predetermined limit. In other words, if the natural rate is found to differ from the Tx indicated rate by more than the predetermined limit, it is deemed that the correlation, i.e., sensitivity function, is not acceptable. In making the comparison, either single cycle values of natural rate and Tx-indicated rate can be compared, or mean values taken over plural cycles can be compared. Following this, the Tx Compare Flag is reset at block 118.

The pacemaker next proceeds to blocks 125 and 126, to determine whether any correlation change is required. At block 125, the pacemaker determines whether any adjustment of the correlation has been signaled from the external programmer, such as illustrated at FIG. 3. If yes, the programmed change in either dT or $dT_{pi}$ is carried out at block 130. If no external rate correlation change is flagged, then the pacemaker proceeds to block 126 and determines whether internally generated data indicates a rate correlation change. This data can come from sensor 52, or it can be produced by the logical analysis made at block 116. If a rate correlation change is indicated, it is made at block 130. At block 131 a check is made to limit the correlation to the predetermined range, preferably 0.5–2.0 ppm/ms.

Returning to block 102, if it is determined that the last interval ended in a sensed QRS, the counter 103 is incremented. At 104, it is determined whether the counter has reached a predetermined number n, representative of an arbitrary number of successive sensed natural heartbeats. If no, the pacing interval and refractory interval are set at 105, and the routine exits. If the counter has reached n, the program branches to block 106, where the counter is reset. At block 108, the pacing interval is adjusted by subtracting the increment $T_T$. $T_T$ may suitably be 10 to 20 ms, sufficient to cause the pacemaker to insert an early stimulus. Thus, depending on the setting of the counter at 104, every n cycles of inhibited operation an early stimulus is delivered so that a Tx-indicated rate determination can be made. At block 109, the limits of $T_{pi}$ are checked, and at block 110 the Tx compare flag is set. The routine then exits, following which a stimulus is delivered, enabling measurement of the QT interval during the next cycle at block 114.

The embodiment of FIG. 4 illustrates a single overdrive stimulus which is specially timed to be delivered just before the next expected spontaneous beat, so as to obtain a Q-T value without the pacer really intervening in the patient's natural rhythm. However, it is to be understood that, if desired, the routine can be changed to continuously decrease $T_{pi}$ over a plurality of cycles until a stimulus is delivered, and to deliver a plurality of stimuli. Thus, for example, following block 106 an "Overdrive" flag may be set which causes the program to branch from block 102 (assuming No response there) to block 108 each pacer cycle until intervention is achieved.

We claim:

1. Demand pacer apparatus for pacing a patient, having stimulus means for delivering stimulus pulses, sensing means for sensing natural heartbeats, and inhibiting means for inhibiting delivery of stimulus pulses when natural heartbeats are sensed, comprising:

QT means for sensing the QT interval of a pacer cycle;

rate means for modifying the rate of delivery of stimulus pulses by said stimulus means as a sensitivity function of said sensed QT interval; and further comprising patient history means for accumulating patient history data over a plurality of pacer cycles, and sensitivity control means automatically operative following cessation of inhibited operation for controlling said sensitivity function in accordance with said accumulated patient history data.

2. The demand pacer apparatus as described in claim 1, wherein said patient history means comprises means for processing said sensed natural heartbeats to obtain the patient's natural rate, and wherein said sensitivity control means further comprises means for changing said sensitivity function only when the pacing rate differs from said obtained natural rate by more than a predetermined limit.

3. The apparatus as described in claim 2, wherein said rate means comprises means for decreasing said pacing interval at a predetermined rate following sensing of a natural heartbeat, whereby said pacer rate rises so that a stimulus pulse is delivered after one or more naturally occurring heartbeats and said QT interval is again measured.

4. Demand pacer apparatus having stimulus means for delivering stimulus pulses, sensing means for sensing natural heartbeats, and inhibiting means for inhibiting delivery of stimulus pulses when natural heartbeats are sensed, comprising:

QT means for sensing the QT interval following each delivered stimulus;

rate means for modifying the pacing interval of said stimulus means as a correlation function of said sensed QT intervals;

overdrive means for decreasing the escape interval of said stimulus means whenever inhibited operation occurs so as to overdrive the natural rate and deliver a stimulus pulse, whereby the QT interval can be sensed and said rate means can modify the pacing interval in accordance with at least one sensed Q-T interval; and pacing interval increasing means for increasing the pacing interval by a predetermined amount d following each delivered stimulus pulse.

5. The demand pacer apparatus as described in claim 4, wherein said overdrive means further comprises means for decreasing said escape interval following each sensed natural heartbeat until a stimulus is delivered.

6. The demand pacer apparatus as described in claim 4, wherein said overdrive means further comprises means for detecting when a plurality of consecutive natural heartbeats has been sensed and means for delivering an early stimulus only when said plurality has been sensed.

7. Demand pacer apparatus having stimulus means for delivering stimulus pulses to a patient and inhibiting means for sensing natural heartbeats and inhibiting delivery of stimulus pulses from said stimulus means when natural heartbeats are sensed, comprising rate means for sensing at least one variable of said patient and for modifying the pacing rate of said stimulus means during delivery of stimulus pulses as a function of said sensed variable, comparison means operative whenever one or more stimulus pulses are delivered by said stimulus means following inhibited operation of said pacer for comparing said modified pacing rate and the rate of natural heartbeats during said inhibited operation, and adjusting means for adjusting said function in accordance with said comparison.

8. The demand pacer apparatus as described in claim 7, wherein said variable is the Q-T interval of said patient and said function is the correlation of pacing rate and Q-T interval.

9. The demand pacer apparatus as described in claim 8, wherein said comparison means comprises means for making said comparison during the pacing cycle following the first delivered stimulus after inhibited operation.

* * * * *